United States Patent [19]
Adrian

[11] Patent Number: 5,593,415
[45] Date of Patent: Jan. 14, 1997

[54] ACOUSTIC CATHETER WITH REDUCED FRICTION DRIVE

[76] Inventor: Sorin Adrian, 311 Fawn Hill La., Penn Valley, Pa. 19072

[21] Appl. No.: 652,124

[22] Filed: May 23, 1996

[51] Int. Cl.⁶ ..................................... A61B 17/32
[52] U.S. Cl. .................. 606/169; 606/171; 606/178; 606/1
[58] Field of Search ..................... 606/169, 171, 606/178, 1, 167, 159; 604/22; 128/330, 24

[56] References Cited

U.S. PATENT DOCUMENTS

| | | | |
|---|---|---|---|
| 5,057,119 | 10/1991 | Clark et al. | 606/169 |
| 5,211,646 | 5/1993 | Alperovich et al. | 606/169 |
| 5,423,797 | 6/1995 | Adrian et al. | 606/1 |

*Primary Examiner*—Michael Powell Buiz
*Assistant Examiner*—Kevin Truong
*Attorney, Agent, or Firm*—William H. Meise

[57] ABSTRACT

An acoustic catheter (10) has a shaft (18) driven by a rotary motor (60). The shaft drives a rotary-to-axial motion converter (30) near the distal end (14) of the catheter. The converter (30) includes a rotary driver (42) with a wavy or sinusoidal bearing surface (36) facing a similarly wavy face (38) of a follower element (44). As the rotary driver (42) rotates, the follower (44) moves axially with a reciprocating motion. High rotational speeds are required to achieve high acoustic frequencies. The high speeds and high acceleration rate of the follower result in frictional forces which cause undesired heating. The heating effects are reduced by a magnetic bearing arrangement associated with the mating bearing surfaces of the rotary driver and follower, which tends to keep them slightly separated, and thereby reduce friction. Other embodiments use magnets to restore the follower to its proximal position following each excursion, and use magnetic thrust bearings for the rotary driver.

13 Claims, 4 Drawing Sheets

ACOUSTIC CATHETER WITH REDUCED FRICTION DRIVE

FIELD OF THE INVENTION

This invention relates to catheters for performing medical procedures, and more particularly to such catheters which use rotary-to-axial motion converters for generating acoustic energy for ablation, angioplasty, and/or other medical procedures.

BACKGROUND OF THE INVENTION

U.S. Pat. No. 5,427,797, issued Jun. 13, 1995 in the name of Adrian et al., describes a rotary-driven acoustic catheter for ablation and angioplasty use. As described therein, a swash-plate-like rotary element located near the distal end of the catheter is driven by a shaft, which, during operation, is in turn driven by a rotary motor. The swash plate element rotates, and a bearing surface portion, which may be its distal surface, describes a reciprocal axial motion. A follower element, which is coupled at its distal end to the biological medium which is to be treated, is biased toward a proximal position by a spring arrangement. Rotation of the rotary driver causes the driver bearing surface to repeatedly urge the follower in a distal direction against the spring force.

The arrangement as described in the abovementioned Adrian et al. patent is capable of generating acoustic energy in the biological medium at a frequency which is a multiple of the rotational rate of the shaft and drive element, in those cases in which the bearing surfaces have more than one round-trip axial excursion for each unit of revolution. In one illustrated embodiment, the rotational driver has a "wavy" surface which provides two back-and-forth axial excursions for each rotation of the rotary driver. The apparatus of the abovementioned Adrian et al. patent, when driven at 200,000 rpm, is capable of generating an acoustic frequency in excess of 6 KHz. without doubling of the frequency by a multiplying driver, and in excess of 13 KHz. when using a doubling-type rotating driver arrangement. Multiplying factors greater than two are described.

When arrangements such as those described in the abovementioned Adrian et al. patent are operated, frictional forces tend to create a substantial amount of heat. Fluid flow through the catheter tends to carry some of the heat away, but it is not always desirable to allow fluid flow. When operated for long periods of time at rotational rates or at high frequencies of operation, heat energy can build up in the region of the rotary-to-axial motion converter, and result in high temperatures. Such high temperatures may adversely affect the operation, or may tend to cause premature failure of the converter. In addition, an excessively high temperature of the converter may injure the patient. Improved acoustic catheters are desired.

SUMMARY OF THE INVENTION

A catheter generates acoustic energy in a biological medium when portions of the catheter are driven by a rotary motor. The catheter includes an elongated body defining a distal end and a proximal end. In general, such a body will be flexible. A shaft extends longitudinally through at least a portion of the body of the catheter. The shaft is associated with a drive coupler located near the proximal end of the body of the catheter, which drive coupler is adapted to be coupled to a rotary motor for causing the shaft to be driven in a rotary manner. A rotary-to-axial motion converter is coupled to the shaft near the distal end of the catheter, and is also coupled to the biological medium, for converting the rotary motion of the shaft into reciprocal axial motion in the form of acoustic energy in the biological medium. The rotary-to-axial motion converter includes (a) a rotary portion coupled to the shaft for being driven in a rotary manner thereby. The rotary portion of the rotary-to-axial motion converter defines a bearing surface which includes portions which, relative to a point fixed on the body of the catheter, move axially in response to rotation of the rotary portion. The axial motion reciprocates in response to the rotation of the shaft. The rotary-to-axial motion converter further includes (b) a follower restrained from rotation relative to the body. The follower includes a bearing surface coupled to the bearing surface of the rotary portion of the rotary-to-axial motion converter, for axial motion of the follower in response to the motion of the bearing surface of the rotary portion of the rotary-to-axial motion converter. The follower, when the catheter is in operation, is also coupled to the biological medium for coupling the axial motion to the biological medium in the form of acoustic waves. The catheter also includes a magnetic arrangement coupled to the rotary portion of the rotary-to-axial motion converter and to the follower, for generating a magnetic force between the bearing surface of the rotary portion of the rotary-to-axial motion converter and the bearing surface of the follower, which force tends to reduce friction between the bearing surfaces of the rotary portion and the follower portion of the rotary-to-axial motion converter.

In a particular embodiment of the invention, the rotary portion of the rotary-to-axial motion converter includes a disk-like or cylinder-like portion centered on the longitudinal axis of the catheter. The disk-like portion has a proximal side coupled to the shaft at its axis. The distal side of the disk-like portion carries the bearing surface of the rotary portion of the rotary-to-axial motion converter. The follower portion of the rotary-to-axial motion converter also includes a second disk-like or cylinder-like portion centered on the longitudinal axis. The disk-like portion of the follower portion of the rotary-to-axial motion Converter carries the bearing portion of the follower on a proximal side, as a result of which the bearing on the distal side of the rotary portion engages the bearing on the proximal side of the follower. In this embodiment, the magnetic arrangement includes (a) a first magnetic pole mounted on the rotary portion of the rotary-to-axial motion converter, oriented so that either a north pole or a south pole (one of a north pole and a south pole) faces the follower. The one of the north and south poles has fields which are symmetric about the longitudinal axis of the catheter. In this particular embodiment, (b) a second magnetic pole is mounted on the follower portion of the rotary-to-axial motion converter. The mounting of the second magnetic pole is such that the same one of the north pole and the south pole faces the rotary portion of the rotary-to-axial motion converter, as a result of which two like magnetic poles face each other on the follower and the rotary portion. The one of the north and south poles which is mounted on the follower has fields which are axially symmetric about the longitudinal axis of the catheter. Since the first and second magnetic poles facing each other are magnetically similar, they tend to repel each other, thereby tending to reduce normal forces acting between the rotary portion and the follower portion of the rotary-to-axial motion converter during operation, which in turn tends to reduce friction therebetween.

In a particular embodiment of the invention, the bearing surface of the rotary portion of the rotary-to-axial motion converter is associated with a distal surface of the rotary portion. The distal surface of the rotary portion has a topology which, when developed about the axis of the catheter, has a sinusoidal variation as a function of rotational angle. In a particularly advantageous version of this embodiment, the bearing surface of the follower which couples to the bearing surface of the rotary portion is a similar sinusoid. This arrangement has the advantage that the mating surfaces are relatively large during those intervals in which the follower is being accelerated distally, to reduce the pressure per unit area on the bearing surfaces, and thereby reduce friction.

In yet another embodiment of the invention, a magnetic arrangement provides the restoring force for the follower. In a further embodiment, a magnetic thrust bearing is used in conjunction with the rotary element.

BRIEF DESCRIPTION OF THE DRAWINGS

FIG. 5a illustrates the spacing between the rotary-driver and the follower element of the arrangement of FIG. 1 attributable to the association of the like magnetic poles therewith, and illustrates the magnetic field structure, while

DESCRIPTION OF THE INVENTION

Figure 1:
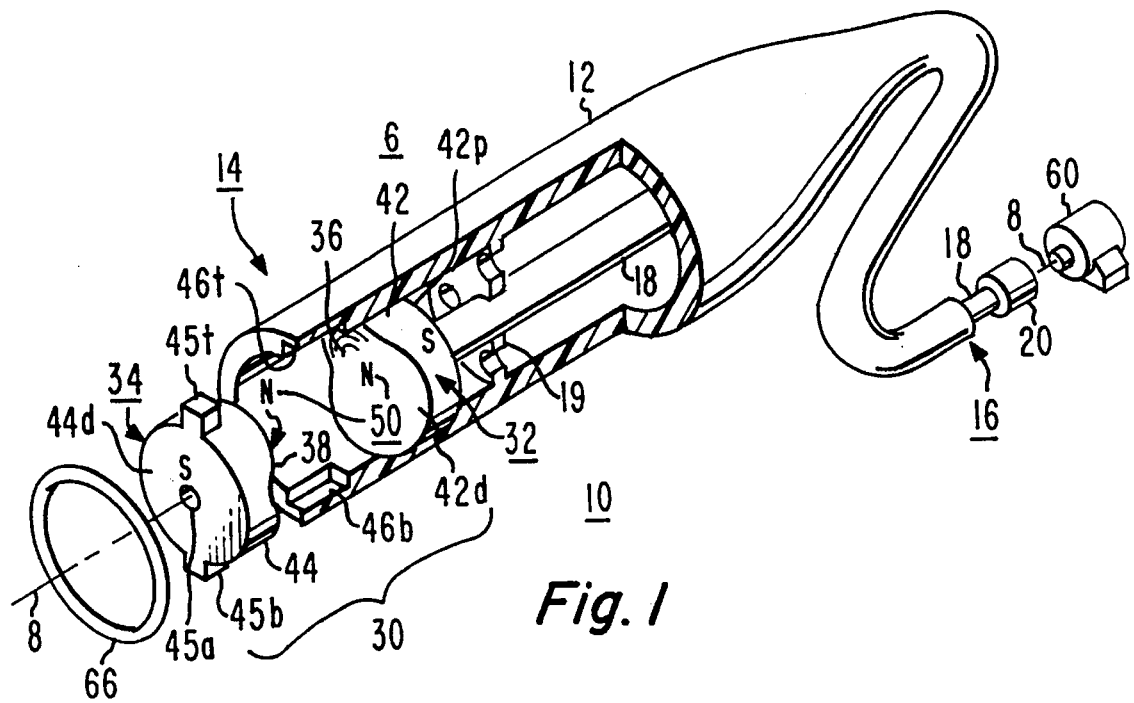
FIG. 1 is a simplified perspective or isometric view, partially cut away and exploded to reveal interior details, of a catheter according to the invention.

FIG. 1 is a simplified perspective or isometric view of a catheter according to the invention. In FIG. 1, catheter 10 includes a body 12 which defines a distal end 14 and a proximal end 16. Distal end 14 of catheter 10 is located within a biological medium designated as 6, and its proximal end 16 is outside the medium. A shaft 18 extends through the a lumen of body 12 of catheter 10 from a rotary-to-axial motion converter 30 to proximal end 16. Shaft 18 protrudes from proximal end 16 of body 12, and a mechanical coupling device illustrated as 20 allows the shaft of a rotary motor 60 to be coupled to shaft 18. As illustrated, motor 60 is separate from catheter 10, but they could be made as a single unit.

The general mode of operation of the arrangement of FIG. 1 is described in detail in the aforementioned Adrian et al. patent. As described generally therein, shaft 18 rotates, supported by a plurality of bushings, one of which is designated as 19, and drives a rotary element 32, which includes a generally disk-like or cylindrical element 42. While the shape is nominally that of a circular cylinder, the device in actual use is likely to be minimized in mass and dimensions so as to appear to be more like a disk than a cylinder, so the term "disk-like" seems appropriate. Shaft 18 joins element 42 on its proximal side 42p. Cylindrical or disk-like element 42 also has a front or distal surface 42d. Disk-like element 42 is restrained against axial motion. As illustrated in FIG. 1, the entirety of distal surface 42d is a bearing surface designated 36. Bearing surface 36 of rotary drive element 32 bears against a corresponding bearing surface 38 of a follower element 34. Follower element 34 is restrained against rotation by protruding top and bottom ears 45t and 45b, which mate with corresponding slots 46t and 46b on the interior wall of body 12. Follower 34 is held in place by a retaining device illustrated as a ring 66, which mates with an annular depression (not illustrated in FIG. 1) in the interior wall of body 12, which may be provide spring tension, thereby allowing axial motion of the follower. Follower 34 may have a central aperture 45a extending therethrough for aspiration purposes. The result of the rotary drive is to cause reciprocating axial motion of the follower element 34. In operation, the distal end of follower element 34 is immersed in, or in contact with, the biological medium 6 to which the acoustic energy is to be applied. Rotation of the rotary element 32 causes the wavy face of bearing 36 to bear against follower 34 to couple axial motion to the follower and, through the follower, acoustic waves into the biological medium.

Figure 2A:
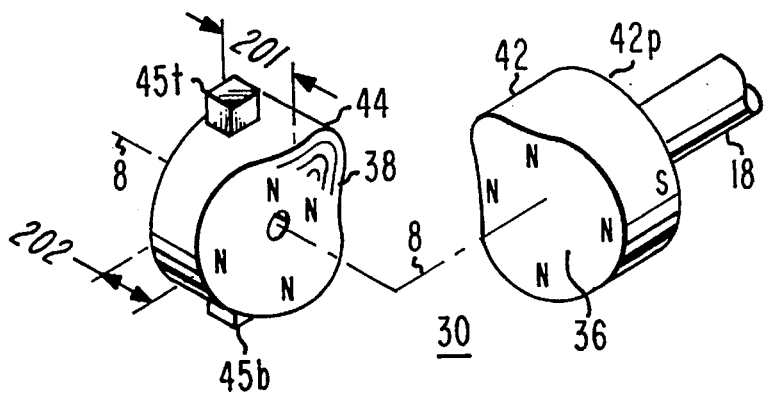
FIG. 2a is a simplified perspective or isometric view of the rotary driver and follower element of the arrangement of FIG. 1, arranged so as to display their mating surfaces and the like magnetic poles on those mating surfaces.
Figure 2B:
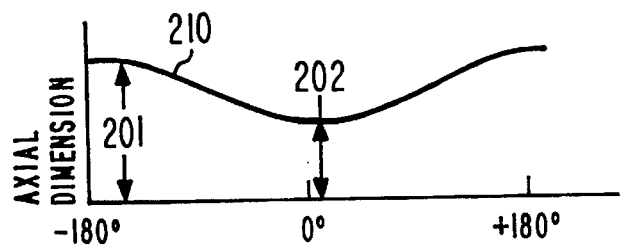
FIG. 2b is a theoretical plot of the axial dimension of a follower element, illustrating the nature of the curvature of the proximal surface thereof if the front surface of the follower element were flat.

As so far described, the arrangement of FIG. 1 is similar to that of the aforementioned Adrian et al. patent. According to an aspect of the invention, frictional forces are reduced by selecting the shape of the bearing surface 38 of the follower 34 to match the shape of the wavy face of bearing surface 36 the driver disk-like element 32. More particularly, FIG. 2a illustrates the mating surfaces of the rotary driver and of the follower. As illustrated, the distal side or end 44d of disk-like portion 44 of follower element 34 is flat, and the proximal surface, which is the bearing surface 38 which bears against the rotary drive element, is wavy. The distal side 44d of element 44 is illustrated as being flat in order to aid in understanding the topology or nature of bearing surface 38, but it should be understood that the distal surface of the follower element may not be flat in order to adjust the acoustic coupling into the biological medium, as described in more detail in the abovementioned Adrian et al. patent. With the understanding that the distal surface 44d is assumed to be flat for ease of understanding, the term "wavy" as applied to bearing surface 38 of the disk-like follower element 44 means that the axial dimension (the dimension parallel to axis 8) of the disk-like element 44, as measured from "flat" distal surface 44d, varies circumferentially about the periphery of disk-like element 44. More particularly, dimension 201 of FIG. 2a represents nearly the largest axial dimension, and dimension 202 is the smallest. These dimensions are illustrated in plot 210 of FIG. 2b, which also illustrates the continuous sinusoidal nature of the change in axial dimension as a function of rotational angle about axis 8 in the illustrated embodiment. With this understanding, it can be seen in FIG. 2a that the greatest proximal extension of bearing surface 38 of disk-like follower element 44 occurs in the same "vertical" plane which contains axis 8 and passes through upper and lower ears 45t and 45b, while the minimum proximal extension occurs in a "horizontal" plane which contains axis 8.

Figure 3A:
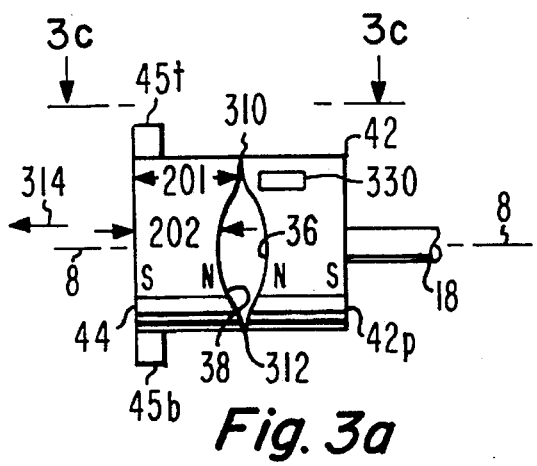
FIG. 3a is a side or elevation view of the rotary driver and follower element of the arrangement of FIG. 1, arranged so as to display how their surfaces mate in one rotational-position of the rotary driver.
Figure 3B:
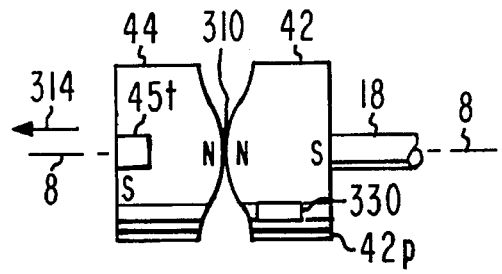
FIG. 3b is a top or plan view of the rotary driver and follower element of the arrangement of FIG. 3a, FIG. 3c is a side or elevation view of the rotary driver and follower element of the arrangement of FIG. 1, arranged so as to display how their surfaces mate in a second rotational position of the rotary driver, displaced by 90° from the rotational position of FIG. 3a, and FIG. 3d is a top or plan view of the rotary driver and follower element of the arrangement of FIG. 3c.

FIGS. 3a, 3b, 3c, and 3d illustrate details of how the mating bearing surfaces 36, 38 of the rotary driver and follower are juxtaposed under various conditions. In FIGS. 3a and 3b, the rotational position of rotary drive disk-like element 42 is such that regions of greatest extension of the mating bearing surfaces 36 and 38 are coincident, so that the bearings make contact only at an upper and lower locations 310, 312, with the result that the disk-like follower 44 is displaced to the left or distally (in the direction of arrow 314) to its maximum extent. In FIGS. 3a and 3b, a marker 330 is provided on rotary drive disk-like element 42 to provide an indication of rotational position.

Figure 3C:
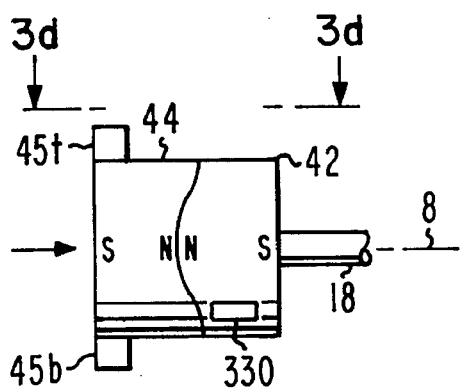
Figure 3D:
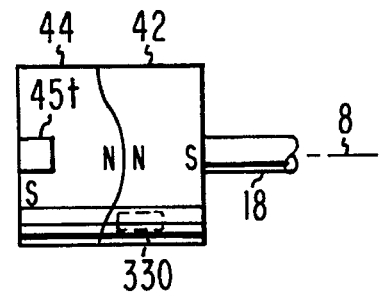

FIGS. 3c and 3d are similar to FIGS. 3a and 3b, respectively, but the rotational position of rotary drive disk-like element 42 is 90° from that of FIGS. 3a and 3b. As a consequence, the "wavy" or sinusoidal surfaces of both the rotary driver and of the follower mate, and the follower reaches its most proximal position. Thus, as the wavy bearing surfaces slide over each other due to rotation of the driver, they reach positions in which they "nest" or "spoon" together to the extent that their curvatures match, as suggested in FIGS. 3c and 3d, and periodically reach a mismatched position, suggested by FIGS. 3a and 3b. The "matched" position corresponds to the most proximal position of the follower element, and the "mismatched" position corresponds to the most distal excursion of the follower.

Figure 4A:
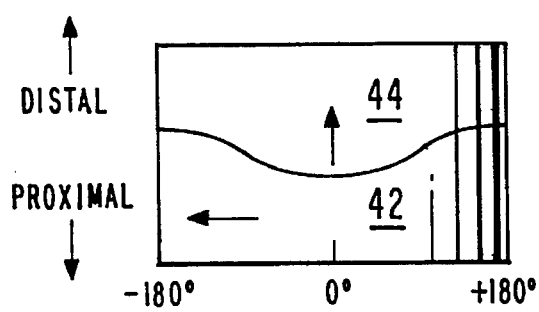
FIG. 4a illustrates the mated condition of the rotary element and follower.
Figure 4B:
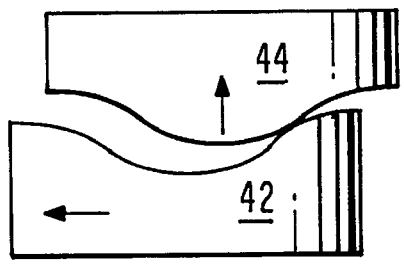
FIG. 4b illustrates a rotary position of the rotary driver which provides less mating.
Figure 4C:
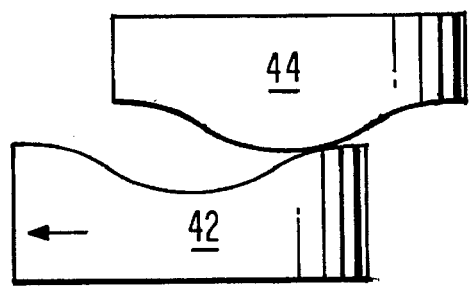
FIG. 4c illustrates the least mating position of the rotary driver.

FIG. 4a illustrates in a developed view (a view illustrating the junction of the surfaces from all angular positions about the axis) the matched condition of the bearing surfaces of rotary driver disk-like element 42 with the bearing surfaces of follower 44. FIG. 4c illustrates the mismatched condition, and FIG. 4b represents a condition part-way between the matched and mismatched conditions. It can be seen that, in the matched position of FIG. 4a, the bearing surfaces are fully mated, and the forces carried by the bearing surfaces are distributed over a relatively large surface area. This is advantageous, because at the instant that the condition of FIG. 4a occurs, the follower is neither advancing in a distal direction nor retreating in a proximal direction. Thus, almost the entire surface is available for supporting the forces required to begin to accelerate the follower distally. As the follower moves distally, it reaches the position illustrated in FIG. 4b, where the maximum acceleration has been passed, and the distal velocity begins to decrease. At this point in the cycle, the normal forces (parallel to axis 8) acting on the bearing surfaces are much less than those in the immediately preceding portion of the cycle. The amount of bearing surface available for supporting the forces is also reduced, as suggested by the position of FIG. 4b. Finally, at the maximum distal excursion of the follower, there is little or no acceleration, and the contact is more of a line contact, which appears as a point contact in the developed view of FIG. 4c. Thus, the amount of bearing surface available for sustaining the forces or loads due to acceleration of the follower are more or less matched by the forces which are applied to the bearings, unlike an arrangement in which contact feet are provided. This, in turn, tends to reduce the frictional forces acting on the bearing surfaces, and tends to reduce wear and heating.

While the illustrated wavy surface is sinusoidal, other surface wave shapes, such as elliptical or exponential, may provide for constant acceleration or other desirable properties.

According to another aspect of the invention, magnetic poles are associated with the rotary driver and with the follower for producing magnetic fields therebetween which tend to keep the bearing surfaces separated, which tends to reduce the normal forces applied to the bearing surfaces, and tends to reduce wear and heating.

Referring once again to FIG. 1, the letters N and S appear on rotary driver disk-like element 42, with the N letter on the distal face 36, and the S near the proximal face 42p. These letters represent north and south magnetic poles, respectively, associated with the rotary driver disk-like element 42. The letters N and S are also associated with disk-like follower element 44, for like purpose. It will be noted that the N poles of the follower and the rotary driver are facing each other. Those skilled in the art know that juxtaposed like magnetic poles tend to repel each other, and that the repulsive force tends to be inversely related to the distance separating the poles. This magnetic repulsion produces a force which tends to keep the two bearing surfaces apart, or, in other words, the magnetic action or repulsion tends to take up some (or all) of the normal forces associated with the load borne by the bearings.

Figure 5A:
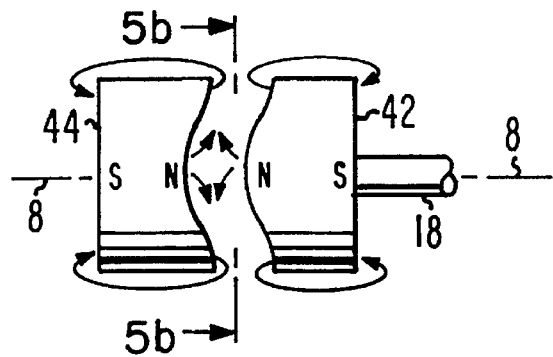
Figure 5B:
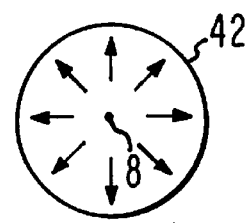
FIG. 5b illustrates the magnetic field of the rotary member as seen from the follower for the case of a single magnetic pole facing the follower.

As illustrated in FIG. 1 and in FIG. 5a, the distal end of the rotary driver is associated with a single north pole designated by the letter N. The construction of FIG. 5a has magnetic field lines such as those illustrated in FIG. 5b. The construction of FIG. 5a could be achieved by making the disk-like rotary driver element 42 from a soft (easily magnetized) magnetic material, such as soft iron. The mass of a soft-iron rotary driver might be greater than that of a rotary driver which was made principally from low-mass plastic, for example, with high-efficiency magnets such as cobalt magnets. However, since rotary drive element only rotates, and does not reciprocate axially, low mass is not mandatory, and a soft-iron construction might be used. On the other hand, the follower 44 must reciprocate, and the forces on the bearings will be related to the mass of the follower. A construction for the follower such as that illustrated in FIG. 5a may not be the most desirable because of the relatively great mass of the requisite soft-iron or other magnetizable core, and it may instead be more desirable to make the follower disk-like element 44 from a low-mass nonmagnetic material, with an array of high-efficiency magnets (large magnetic forces per unit mass) fitted therein, as illustrated in FIG. 6. As illustrated in FIG. 6b, the magnetic fields of such a multipole structure are also symmetric about the longitudinal axis 8. FIG. 2a also illustrates that the proximal surface of the follower could include four N poles, symmetrically spaced 90° about the axis. The more poles that are used, the more uniform the repulsion will be as a function of rotational angle of the rotary element.

Figure 6A:
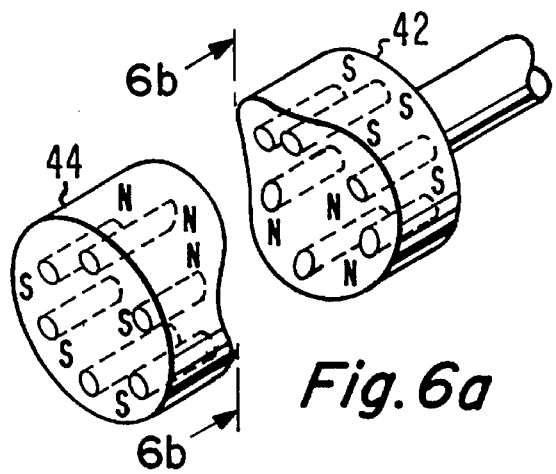
FIG. 6a illustrates rotary drive and follower members which have a plurality of magnetic poles associated with each mating face.
Figure 6B:
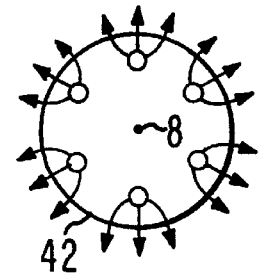
FIG. 6b illustrates the symmetric magnetic fields.
Figure 7:
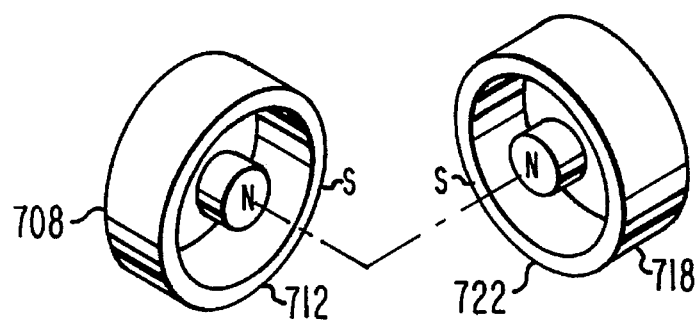
FIG. 7 illustrates how magnetized cup-cores may present two separate magnetic poles for repulsion.
Figure 8:
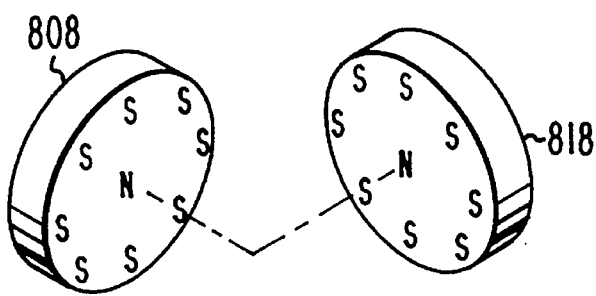
FIG. 8 illustrates a surface-magnetized version of the arrangement of FIG. 7.

FIG. 7 illustrates a magnet arrangement which may provide greater magnetic force than the arrangements of FIGS. 5a and 6a. In FIG. 7, the magnetic material 708 associated with the follower (not illustrated in FIG. 7) is in the shape of a well known "cup core," with the center or core portion 710 magnetized with one magnetic polarity, illustrated as N, and with the edge of the peripheral cup 712 having the opposite magnetic pole S. When the first such cup-core shaped magnet 708 is juxtaposed with a second similar cup-core member 718 having its core 720 poled N and its peripheral wall poled S, one on the rotary element and one on the follower, the mutual repulsion is provided by both the magnetic poles, rather than by just one. This arrangement provides more magnetic repulsion for the same amount of magnetic material. FIG. 8 illustrates simple disks of magnetizable material which are surface-magnetized with magnetic poles corresponding to the magnetic poles of the arrangement of FIG. 7; the same fields are available, and hence the same forces, but the surface-magnetized disk is smaller and lighter that the cup-shaped elements of FIG. 7.

Figure 9A:
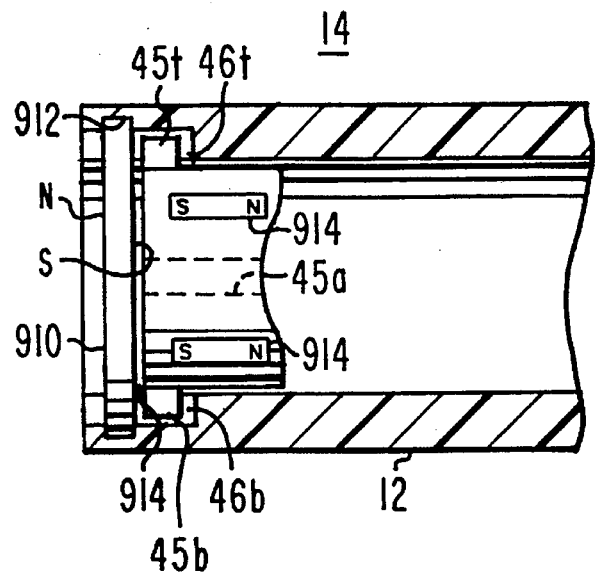
FIG. 9a side elevation view of the distal end of a catheter according to the invention, cut away to reveal interior details of a magnetic follower restorer in its proper position for coacting with the magnetic fields of the follower.
Figure 9B:
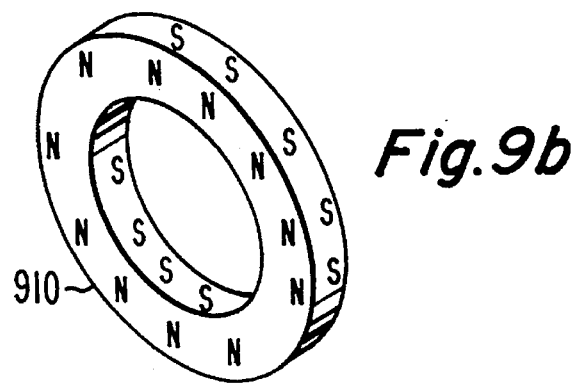
FIG. 9b illustrates the magnetic field structure of the restorer.

In FIG. 9a, the distal end 14 of a catheter according to the invention is illustrated in cut-away view. In the arrangement of FIG. 9a, the distal end of the follower has an S magnetic pole characteristic because of the rod magnets 914 in the body of follower disk-like element 44 provide an N pole to the distal side of the follower element. The retainer ring which holds the follower in place in FIG. 9a, which in the arrangement of FIG. 1 is a spring element 66, is instead a magnetized ring 910. Magnetized ring 910 is held in place by an annular circumferential groove 912 defined in the inner surface of the lumen of body 12 of catheter 10. In this position, ring 910 acts as a mechanical bar to prevent the follower from falling out, just as a split-ring retainer might. Instead of being a Belleville washer or some other type of spring element, ring 910 is magnetized as illustrated in FIG. 9b, with an N pole on its distal end and an S pole on its proximal end. The proximal end of the ring 910 is adjacent to the distal end of follower element 44, and there are therefore two S poles facing each other at the distal end of the follower. This arrangement tends to repel the follower in a proximal direction, just as a spring element would; however, it is less likely to have a high-frequency limitation due to resonant behavior, as a spring might.

Figure 10:
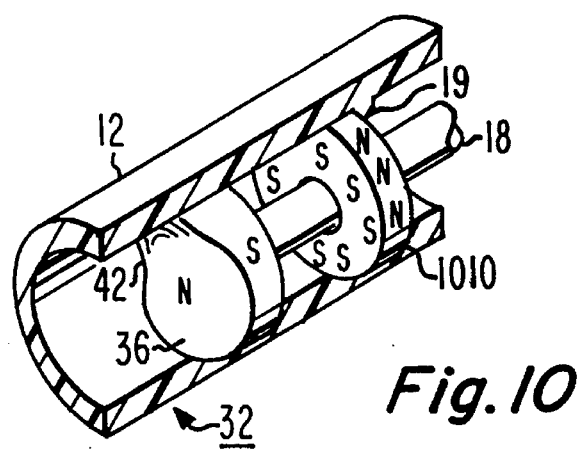
FIG. 10 is a simplified view of a portion of the arrangement of FIG. 1, illustrating the use of a magnetic thrust bearing in conjunction with the rotary drive element.

FIG. 10 illustrates a portion of the arrangement of FIG. 1, illustrating rotary drive element 32 in the form of a disk-like element 42 with a north (N) pole adjacent its distal face and a south (S) pole adjacent its proximal face. As illustrated in FIG. 10, a thrust bearing in the form of a magnetized ring 1010 is mounted proximate to the proximal end of the rotary drive element 32; the separation between ring 1010 and the rotary drive element 32 is exaggerated for clarity. The side or end of magnetized ring 1010 which is proximate to rotary drive element 32 is poled S, so as to provide a repulsive force which tends to prevent the rotary drive element from being moved in a proximal direction under the impetus of the forces resulting from driving the follower.

A catheter (10) according to the invention generates acoustic energy in a biological medium (6) when portions of the catheter are driven by a rotary motor (60). The catheter (10) includes an elongated body (12) defining a distal end (14) and a proximal end (16). In general, such a catheter body (12) will be flexible. A shaft (18) extends longitudinally through at least a portion of the body (12) of the catheter (10). The shaft (18) is associated with a drive coupler (20) located near the proximal end (16) of the body (12) of the catheter, which drive coupler is adapted to be coupled to the rotary motor (60) for causing the shaft (18) to be driven in a rotary manner. A rotary-to-axial motion converter (30) is coupled to the shaft near the distal end (14) of the catheter, and is also coupled to the biological medium (6), for converting the rotary motion of the shaft (18) into reciprocal axial motion in the form of acoustic energy in the biological medium. The rotary-to-axial motion converter (30) includes (a) a rotary portion (32) coupled to the shaft for being driven in a rotary manner thereby. The rotary portion (32) of the rotary-to-axial motion converter defines a bearing surface (36) which includes portions which, relative to a point fixed on the body (12) of the catheter (10), move axially in response to rotation of the rotary portion (32). The axial motion reciprocates in response to the rotation of the shaft (18). The rotary-to-axial motion converter (30) further includes (b) a follower (34) restrained from rotation relative to the body (12). The follower (34) includes a bearing surface (38) coupled to the bearing surface (36) of the rotary portion (32) of the rotary-to-axial motion converter (30), for axial motion of the follower (34) in response to the motion of the bearing surface (36) of the rotary portion (32) of the rotary-to-axial motion converter (30). The follower (34), when the catheter (10) is in operation, is also coupled to the biological medium (6) for coupling the axial motion to the biological medium in the form of acoustic waves. The catheter also includes a magnetic arrangement (50) coupled to the rotary portion (32) of the rotary-to-axial motion converter (30) and to the follower (34), for generating a magnetic force between the bearing surface (36) of the rotary portion (32) of the rotary-to-axial motion converter (30) and the bearing surface (38) of the follower (34), which force tends to reduce friction between the bearing surfaces (36, 38) of the rotary portion (32) and the follower portion (34) of the rotary-to-axial motion converter (30).

In a particular embodiment of the invention, the rotary portion (32) of the rotary-to-axial motion converter (30) includes a generally disk-like or cylinder-like portion (42) centered on the longitudinal axis (8) of the catheter (10). The disk-like portion (42) has a proximal side (42p) coupled at its axis (8) to the shaft (18). The distal side (42d) of the disk-like portion (42) carries the bearing surface (36) of the rotary portion (32) of the rotary-to-axial motion converter (30). The follower portion (34) of the rotary-to-axial motion converter (30) also includes a second disk-like or cylinder-like portion (44) centered on the longitudinal axis (8). The disk-like portion (44) of the follower portion (34) of the rotary-to-axial motion converter (30) carries the bearing portion of the follower (34) on a proximal side (38) thereof, as a result of which the bearing on the distal side (42d) of the rotary portion (32) engages the bearing on the proximal side (38) of the follower (34). In this embodiment, the magnetic arrangement includes (a) a first magnetic pole mounted on the rotary portion of the rotary-to-axial motion converter, oriented so that either a north pole or a south pole (one of a north pole and a south pole) faces the follower. The one of the north and south poles has fields which are symmetric about the longitudinal axis of the catheter. In this particular embodiment, (b) a second magnetic pole is mounted on the follower portion of the rotary-to-axial motion converter. The mounting of the second magnetic pole is such that the same one of the north pole and the south pole faces the rotary portion of the rotary-to-axial motion converter, as a result of which two like magnetic poles face each other on mutually facing portions of the follower and the rotary portion. The one of the north and south poles which is mounted on the follower has fields which are axially symmetric about the longitudinal axis of the catheter. Since the first and second magnetic poles facing each other are magnetically similar, they tend to repel each other, thereby tending to reduce normal forces acting between the rotary portion and the follower portion of the rotary-to-axial motion converter during operation, which in turn tends to reduce friction therebetween.

In a particular embodiment of the invention, the bearing surface of the rotary portion of the rotary-to-axial motion converter is associated with a distal surface of the rotary portion. The distal surface of the rotary portion has a topology which, when developed about the axis of the catheter, has a sinusoidal variation as a function of rotational angle. In a particularly advantageous version of this embodiment, the bearing surface of the follower which couples to the bearing surface of the rotary portion is a similar sinusoid. This arrangement has the advantage that the mating surfaces are relatively large during those intervals in which the follower is being accelerated distally, to reduce the pressure per unit area on the bearing surfaces, and thereby reduce friction.

In yet another embodiment of the invention, a magnetic arrangement provides the restoring force for the follower. In a further embodiment, a magnetic thrust bearing is used in conjunction with the rotary element.

Other embodiments of the invention will be apparent to those skilled in the art. For example, a catheter according to the invention may include a lumen extending from the distal to the proximal end for introduction of medication into the patient, or for aspirating fluids during operation. Aspiration of fluids may be accomplished in the same manner as that described in the abovementioned U.S. Pat. No. 5,427 797. While no additional lumens have been described in relation to the catheter according to the invention, lumens may be provided in conjunction with a catheter according to the invention for any of the conventional purposes such as aspiration, and other devices may also be used in conjunction therewith or integrated therewith, such as fiber-optic scopes, optical fibers for lasers, guide wires, balloons, antennas or transmitting devices for heating or for locating, sensors, and the like. While the sinusoidal surfaces of the bearings have been illustrated as having a single sinusoidal variation as a function of 360° rotation, it would also be possible to have multiple sinusoidal variations in 360°, in order to obtain frequency multiplication. As mentioned, the wariness of the bearing surfaces of the rotary drive elements and the follower may follow some curvature other than sinusoidal, and the wariness of the bearing surfaces need not match exactly. While the number of magnetic poles associated with the rotary element may equal the number associated with the follower, they may have different numbers of magnetic poles.

What is claimed is:

1. A catheter for generating acoustic energy in a biological medium when portions of said catheter are driven by a rotary motor, said catheter comprising:

an elongated body defining a distal end and a proximal end;

a shaft extending longitudinally through at least a portion of said body, said shaft being associated with drive coupling means located near said proximal end of said body of said catheter, which drive coupling means is adapted to be coupled to a rotary motor for causing said shaft to be driven with a rotary motion;

rotary-to-axial motion conversion means coupled to said shaft near said distal end of said catheter, and also coupled-to said biological medium, for converting said rotary motion into reciprocal axial motion in the form of acoustic energy, said rotary-to-axial motion conversion means including (a) a rotary portion coupled to said shaft for being driven in a rotary manner thereby, said rotary portion of said rotary-to-axial motion conversion means also defining a bearing surface including portions which, relative to a point fixed on said body of said catheter, move axially in response to rotation of said rotary portion, said rotary-to-axial motion conversion means further including (b) follower means restrained from rotation relative to said body, said follower means including a bearing surface coupled to said bearing surface of said rotary portion of said rotary-to-axial motion conversion means, for axial motion in response to said motion of said bearing surface of said rotary portion of said rotary-to-axial motion conversion means, said follower means, when said catheter is in operation, also being coupled to said biological medium for coupling said axial motion to said biological medium in the form of acoustic waves; and magnetic means coupled to said rotary portion of said rotary-to-axial motion conversion means and to said follower means, for generating a magnetic force between said bearing surface of said rotary portion of said rotary-to-axial motion conversion means and said bearing surface of said follower means which tends to reduce friction between said bearing surfaces of said rotary portion and said follower portion of said rotary-to-axial motion conversion means.

2. A catheter according to claim 1, wherein:

said rotary portion of said rotary-to-axial motion conversion means comprises a disk-like portion centered on an axis, said disk-like portion also including a proximal side coupled at said axis to said shaft, and a distal side which defines said bearing surface;

said follower portion of said rotary-to-axial motion conversion means comprises a disk-like portion centered about said axis, said disk-like portion of said follower portion of said rotary-to-axial motion conversion means defining said bearing surface of said follower means on a proximal side thereof, whereby at least a portion of said bearing surface on said distal side of said rotary portion engages said bearing surface on said proximal side of said follower means; and said magnetic means comprises (a) a first magnetic pole mounted on said rotary portion of said rotary-to-axial motion conversion means, the mounting of said first magnetic pole being oriented so that one of a north pole and a south pole faces said follower means, said one of said north and south poles having fields which are axially symmetric about said axis; and (b) a second magnetic pole mounted on said follower portion of said rotary-to-axial motion conversion means, the mounting of said second magnetic pole being oriented so that said one of said north pole and said south pole faces said rotary portion of said rotary-to-axial motion conversion means, said one of said north and south poles having fields which are axially symmetric about said axis, whereby said first and second magnetic poles facing each other are magnetically similar, and tend to repel each other, thereby tending to reduce normal forces acting between said rotary portion and said follower portion of said rotary-to-axial motion conversion means, which in turn tends to reduce friction therebetween.

3. A catheter according to claim 1, wherein said bearing surface of said rotary portion of said rotary-to-axial motion conversion means includes a distal surface of said rotary portion, which distal surface of said rotary portion has a wavy topology which.

4. A catheter according to claim 1, wherein said wavy topology, when developed about said axis of said catheter, has a sinusoidal variation as a function of rotational angle; and wherein said bearing surface of said follower means of said rotary-to-axial motion conversion means includes a proximal surface of said follower means, which proximal surface of said follower means has a topology with a sinusoidal variation as a function of rotational angle similar to that of said bearing surface of said rotary portion, so that, in at least one rotational position of said rotary portion, said bearing surfaces nest together.

5. A catheter according to claim 1, wherein said follower is restored to its proximal position by the repulsive force of a magnet located distally of said follower.

6. A catheter according to claim 1, further comprising a magnetic thrust element associated with said rotary portion, for tending to prevent axial motion of said rotary portion in a proximal direction.

7. A catheter according to claim 1, further comprising magnetic restoring means coupled to said follower means, for tending to urge said follower means in a proximal direction.

8. A catheter for generating acoustic energy in a biological medium when portions of said catheter are driven by a rotary motor, said catheter comprising:

an elongated body defining distal and proximal ends, and a longitudinal axis;

a shaft extending longitudinally through said body, and including drive coupling means near said proximal end of said catheter, adapted to be coupled to a rotary motor for being driven with a rotary motion thereby;

rotary-to-axial motion conversion means coupled to the distal end of said shaft and to said biological medium, for converting said rotary motion into reciprocal axial motion in the form of acoustic energy, said rotary-to-axial motion conversion means including a rotary element coupled to said distal end of said shaft for being rotated thereby, and a follower fixed against rotation, each of said rotary element and said follower having mating bearing surfaces, each of said mating bearing surfaces, when developed about said axis, defining a wavy variation of axial position of said surface, whereby at a first rotational position of said rotary element, said bearing surfaces mate, and said follower takes its most proximate position, and whereby at a second rotational position of said rotary element, which is at a particular angle from said first position, said bearing surfaces do not mate, and said follower takes on its most distal position.

9. A catheter according to claim 8, wherein said wavy variation includes at least one sinusoidal variation in 360°.

10. A catheter according to claim 8, further comprising magnetic means associated with said rotary element and with said follower, for creating a magnetic repulsion between said rotary element and said follower which tends to reduce friction between said rotary element and said follower.

11. A catheter according to claim 9, wherein said magnetic means comprises a magnetic pole associated with said bearing surface of said rotary element, and a like-polarity pole associated with said bearing surface of said follower.

12. A catheter according to claim 10, wherein said magnetic pole is a north magnetic pole.

13. A catheter according to claim 8, wherein said follower is restored to its proximal position with the aid of a magnet located distally relative to said follower.

* * * * *